US012446900B2

(12) United States Patent
Miller et al.

(10) Patent No.: US 12,446,900 B2
(45) Date of Patent: Oct. 21, 2025

(54) PROTECTIVE RESECTION GUIDE FOR ROBOTICALLY ASSISTED ARTHROPLASTY

(71) Applicant: Zimmer, Inc., Warsaw, IN (US)

(72) Inventors: David Miller, Warsaw, IN (US); Kaitlyn Lasko, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 405 days.

(21) Appl. No.: 17/974,038

(22) Filed: Oct. 26, 2022

(65) Prior Publication Data

US 2023/0127066 A1 Apr. 27, 2023

Related U.S. Application Data

(60) Provisional application No. 63/272,534, filed on Oct. 27, 2021.

(51) Int. Cl.
*A61B 17/17* (2006.01)
*A61B 34/30* (2016.01)

(52) U.S. Cl.
CPC ............ *A61B 17/175* (2013.01); *A61B 34/30* (2016.02); *A61B 17/17* (2013.01)

(58) Field of Classification Search
CPC ..... A61B 17/15; A61B 17/151; A61B 17/152; A61B 17/154; A61B 17/155; A61B 17/157; A61B 17/17; A61B 17/1703; A61B 17/1707; A61B 17/1714; A61B 17/1717; A61B 17/1721; A61B 17/1725; A61B 17/1728; A61B 17/1732; A61B 17/1735; A61B 17/1739; A61B 17/1742; A61B 17/1746; A61B 17/175; A61B 17/1753; A61B 34/30; A61B 34/32; A61B 34/35; A61B 34/37
See application file for complete search history.

(56) References Cited

U.S. PATENT DOCUMENTS

| | | | | |
|---|---|---|---|---|
| 6,209,886 | B1 * | 4/2001 | Estes | B23B 51/126 279/143 |
| 10,555,782 | B2 * | 2/2020 | Morard | A61B 90/11 |
| 11,298,197 | B2 * | 4/2022 | Dumpe | G16H 50/30 |
| 11,844,582 | B2 * | 12/2023 | Dumpe | G16H 10/20 |
| 11,931,052 | B2 * | 3/2024 | Sweeney | A61B 17/1633 |
| 11,986,258 | B2 * | 5/2024 | Lawrie | A61B 34/30 |
| 12,186,042 | B2 * | 1/2025 | Dumpe | G16H 40/67 |
| 12,201,307 | B2 * | 1/2025 | Sweeney | A61B 5/40 |
| 12,239,399 | B2 * | 3/2025 | Lawrie | A61B 17/1633 |
| 2014/0236160 | A1 * | 8/2014 | Barsoum | A61B 17/1746 606/91 |
| 2016/0235492 | A1 * | 8/2016 | Morard | A61B 17/1703 |

(Continued)

FOREIGN PATENT DOCUMENTS

| | | | | |
|---|---|---|---|---|
| EP | 3892209 A1 * | 10/2021 | | A61B 17/14 |
| WO | WO-2016131903 A1 * | 8/2016 | | A61B 17/1671 |

*Primary Examiner* — Eric S Gibson
(74) *Attorney, Agent, or Firm* — Schwegman Lundberg & Woessner, P.A.

(57) ABSTRACT

A cutting guide for a robotic surgical system can include a cutting block defining a guide surface to guide a cutting instrument along a trajectory, an arm connected to the cutting block to couple the cutting guide to the robotic surgical system, and a first retractable shield configured to extend from a first retracted position clear of the trajectory to a second deployed position within the trajectory.

18 Claims, 8 Drawing Sheets

(56) References Cited

U.S. PATENT DOCUMENTS

| | | | | |
|---|---|---|---|---|
| 2017/0312035 | A1* | 11/2017 | May | A61B 50/33 |
| 2019/0269469 | A1* | 9/2019 | Bush, Jr. | A61B 34/74 |
| 2020/0093555 | A1* | 3/2020 | Flatt | A61B 34/30 |
| 2020/0297357 | A1* | 9/2020 | Cameron | A61B 90/03 |
| 2021/0093333 | A1* | 4/2021 | Chappuis | A61B 34/30 |
| 2022/0039886 | A1* | 2/2022 | Dumpe | G16H 50/50 |
| 2022/0104901 | A1* | 4/2022 | Lawrie | A61B 34/20 |
| 2022/0233258 | A1* | 7/2022 | Dumpe | G16H 40/67 |
| 2022/0257263 | A1* | 8/2022 | Chappuis | A61B 34/74 |
| 2023/0112058 | A1* | 4/2023 | Sweeney | A61B 90/04<br>606/80 |
| 2023/0127066 | A1* | 4/2023 | Miller | A61B 34/30<br>606/89 |
| 2024/0074825 | A1* | 3/2024 | Dumpe | A61B 17/162 |
| 2024/0188967 | A1* | 6/2024 | Sweeney | A61B 5/40 |

* cited by examiner

PROTECTIVE RESECTION GUIDE FOR ROBOTICALLY ASSISTED ARTHROPLASTY

CLAIM OF PRIORITY

This application claims the benefit of U.S. Provisional Patent Application Ser. No. 63/272,534, filed on Oct. 27, 2021, the benefit of priority of which is claimed hereby, and which is incorporated by reference herein in its entirety.

BACKGROUND

A total hip arthroplasty, or hip replacement, procedure involves resecting or cutting the femoral neck to shape the femur to receive an implant. The femur can be cut by translating a rotating or reciprocating cutting instrument along a cutting guide positioned proximally to a patient's femoral neck, such as to guide resection of the femoral neck along a preoperatively or intraoperatively planned trajectory.

SUMMARY/OVERVIEW

A total hip arthroplasty can first involve making an access incision in a hip region of a patient, into which a cutting guide configured for intra-procedurally guiding translation of a cutting instrument along a resection trajectory can be inserted to access the femoral neck of the patient. However, femoral neck resection can be a challenging and time-consuming operation for a surgeon, and various patient outcomes can be significantly diminished if the resection is imprecisely or otherwise inadequately performed. For example, precisely positioning and maintaining the cutting guide in a location proximal to the femoral neck so as to guide a cutting instrument along a preoperatively determined trajectory during resection can be difficult to achieve. Further, the cutting instrument can damage various soft tissues located proximally to the femoral neck, such as when translated along the cutting guide, if not guided with care or inhibited from such movement by the guide. Such damage can potentially reduce patient outcomes, lengthen recovery time, and increase post-operative pain and discomfort.

The present disclosure can help to address the above issues, among others, such as by providing a cutting guide capable of protecting various soft tissues of a patient located proximate the patient's femoral neck and helping to maintain alignment of the cutting guide with a preoperatively determined trajectory during resection of the femoral neck. For example, the cutting guide can include a retractable shield configured to limit translation of a cutting instrument relative to the cutting guide. The retractable shield can be translated by a user from a first retracted position to a second deployed position to secure the cutting guide to the femoral neck. The user can then translate the cutting instrument along the cutting guide to cut the femoral neck until the cutting instrument contacts the retractable shield, such as to inhibit the cutting instrument from contacting and thereby damaging the soft tissues during resection.

Additionally, the cutting guide can be coupled to a robotic surgical arm to reduce the duration and increase the precision of a total hip arthroplasty procedure, such as to further improve patient outcomes. For example, the robotic surgical arm can help to increase the speed and improve the accuracy at which the cutting guide can be positioned proximal to the femoral neck in alignment with a preoperatively determined trajectory. The robotic surgical arm can further improve the stability of the cutting guide, relative to a human hand, such as to maintain the cutting guide in a precise location for an extended period of time during a total hip arthroplasty procedure. While the above overview and following examples are discussed in view of a hip arthroplasty procedure, the described cutting guide and robotic surgical arm can be utilized in other similar arthroplasty procedures, such as in various aspects of knee or shoulder arthroplasty procedures.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
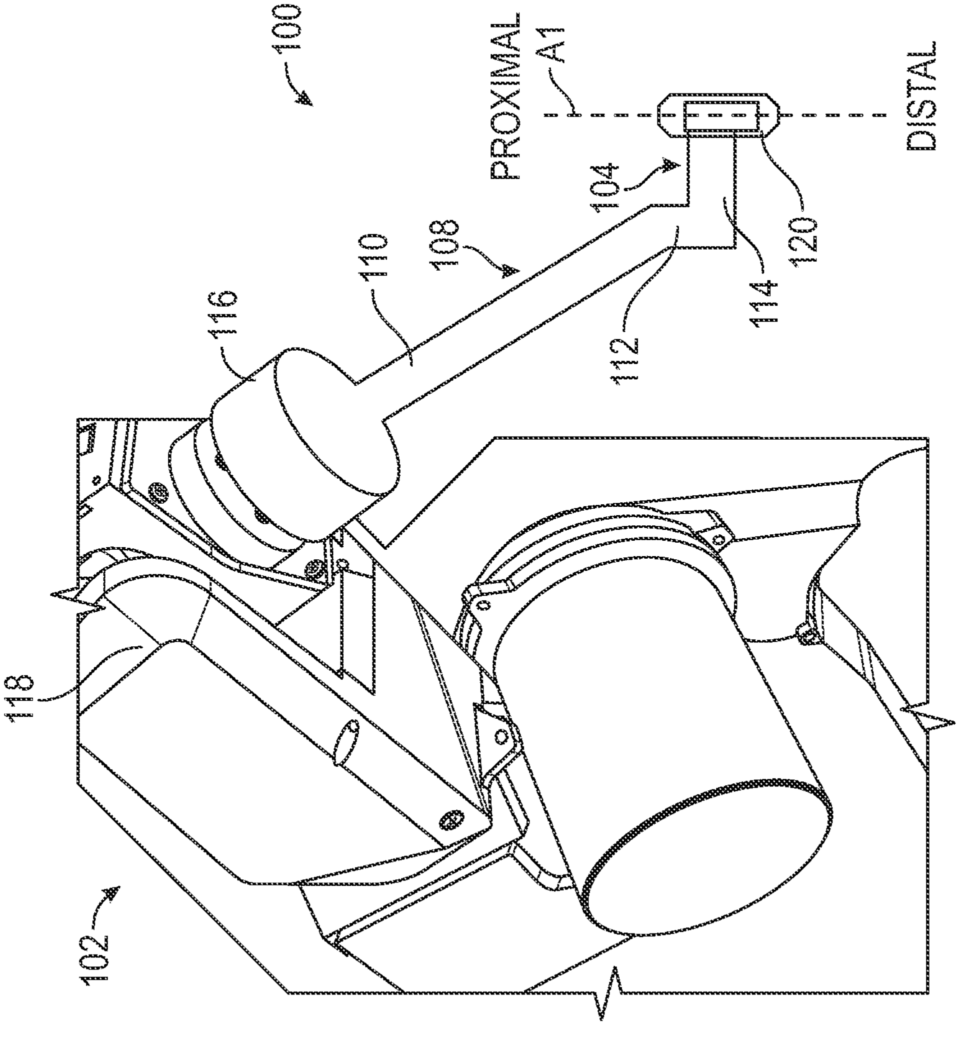
FIG. 1 illustrates a perspective view of a cutting guide connected to a robotic surgical system.

FIG. 1 illustrates a perspective view of a cutting guide 100 connected to a robotic surgical system 102. Also shown in FIG. 1 is a first axis A1, and orientation indicators Proximal and Distal relating to relative positions along the cutting guide 100. The cutting guide 100 can include a cutting block 104. The cutting block 104 can be configured to guide a cutting instrument, such as a rotating or reciprocating cutting blade. For example, the cutting block 104 can define a guide surface 106 (FIGS. 2A-3B). The guide surface 106 can be a planar surface configured to be contacted by the cutting instrument, such as to guide the cutting instrument along a resection trajectory. The cutting guide 100 can include an arm 108. The arm 108 can be configured to connect the cutting block 104 to the robotic surgical system 102. For example, the arm 108 can include a first portion 110, a second portion 112, and a third portion 114.

The first portion 110 can be configured to couple the arm 108 to the robotic surgical system 102. For example, the first portion 110 can engage with various styles of a pre-existing end effector coupler 116 of a robotic surgical arm 118 of the robotic surgical system 102. In one example, the robotic surgical arm 118 can be a 6 degree-of-freedom (DOF) robot arm, such as the ROSA® robot from Medtech, a Zimmer Biomet Holdings, Inc. company. The robotic surgical arm 118 can adjust and maintain a position of the cutting guide 100 before or during a surgical procedure. For example, the robotic surgical arm 118 can be used to precisely position the guide surface 106 of the cutting block 104 in a planned position proximal to a patient's femur, such as in alignment with a resection trajectory in accordance with a preoperative plan. The robotic surgical arm 118 can help to control the position and movement of the cutting guide 100 relative to a patient more precisely and steadily than a human hand.

The second portion 112 of the arm 108 can extend from the first portion 110. For example, the second portion 112 can extend at an obtuse angle from the first portion 110, such as laterally and distally toward the cutting block 104 to form an acute angle with the first axis A1. The third portion 114 can extend from the second portion 112 to connect the arm 108 to the cutting block 104. For example, the third portion 114 can extend at an obtuse angle from the second portion 112, such as orthogonally to the cutting block 104 to form a right angle with the first axis A1. In some examples, the third portion 114 can form a concave shape to vertically or laterally offset the cutting block 104 from the second portion 112, such as enable the arm 108 to conform to or avoid various anatomical features of a patient during an arthroplasty procedure. The first portion 110, the second portion 112, or the third portion 114 can be a solid or a hollow shaft defining a square, circular, triangular, or rectangular cross-sectional shape, or the like. The first portion 110, the second portion 112, and the third portion 114 can be formed as separate connectable components or can be integrally formed as a single unit. In some examples, the arm 108 can include one or a combination of the first portion 110, the second portion 112, or the third portion 114 to connect the cutting block 104 to the end effector coupler 116 of the robotic surgical arm 118.

The cutting guide 100 can include a first retractable shield 120. The first retractable shield can be configured to resist contact by a cutting instrument. The first retractable shield 120 can be connected to the cutting block 104. For example, the first retractable shield 120 can be proximally and distally translatable along the cutting block, such that the first retractable shield 120 can be translated between a first retracted position (shown in FIG. 2A) and a second deployed position (shown in FIG. 2B). In the first retracted position, the first retractable shield 120 can be located clear of a resection trajectory e.g., a vector or plane), defined by the guide surface 106. In the second deployed position, the first retractable shield 120 can be located within the resection trajectory defined by the guide surface 106, such as on the far or distal side of a femoral head. The first retractable shield 120 can thereby limit translation of a cutting instrument along the or otherwise relative to the guide surface 106.

During an arthroplasty procedure, various aspects of femoral head resection can be performed using the cutting guide 100 or the robotic surgical system 102. For example, a user can locate the cutting block 104 proximal to a femoral neck 122 (shown in FIGS. 2A-2B) of a patient, such as by operating the robotic surgical arm 118 to position the guide surface 106 of the cutting block 104 parallel to a preoperatively determined resection trajectory. In some procedures, the robotic surgical arm 118 can further precisely retain the cutting guide 100 in such a position for an extended length of time. A user can translate the first retractable shield 120 from the first retracted position to the second deployed position to secure the cutting block 104 to the femoral neck, such as to form an encirclement zone around a portion of the femoral neck 122 located therebetween, thereby preventing engagement of the cutting instrument with soft tissue distal of the first retractable shield 120.

A user can position a cutting instrument along the cutting block 104, such as in contact with the guide surface 106. A user can then activate and translate the cutting instrument along the guide surface 106, such as to resect the femoral neck 122 (FIG. 2A) along the resection trajectory defined by the guide surface 106. During resection, the first retractable shield 120 can limit lateral or vertical translation of the cutting instrument along the guide surface 106 or otherwise relative to the cutting block 104, such as to prevent the cutting instrument from contacting and damaging soft tissue of the patient. After the arthroplasty procedure, a user can decouple the cutting guide 100 from the robotic surgical arm 118. The cutting guide 100, or various components thereof, can subsequently be cleaned and sterilized in an autoclave, or via another method, in preparation for a future arthroplasty procedure. The cutting guide 100 can thereby help perform one or more operations of an arthroplasty procedure.

Figure 2B:
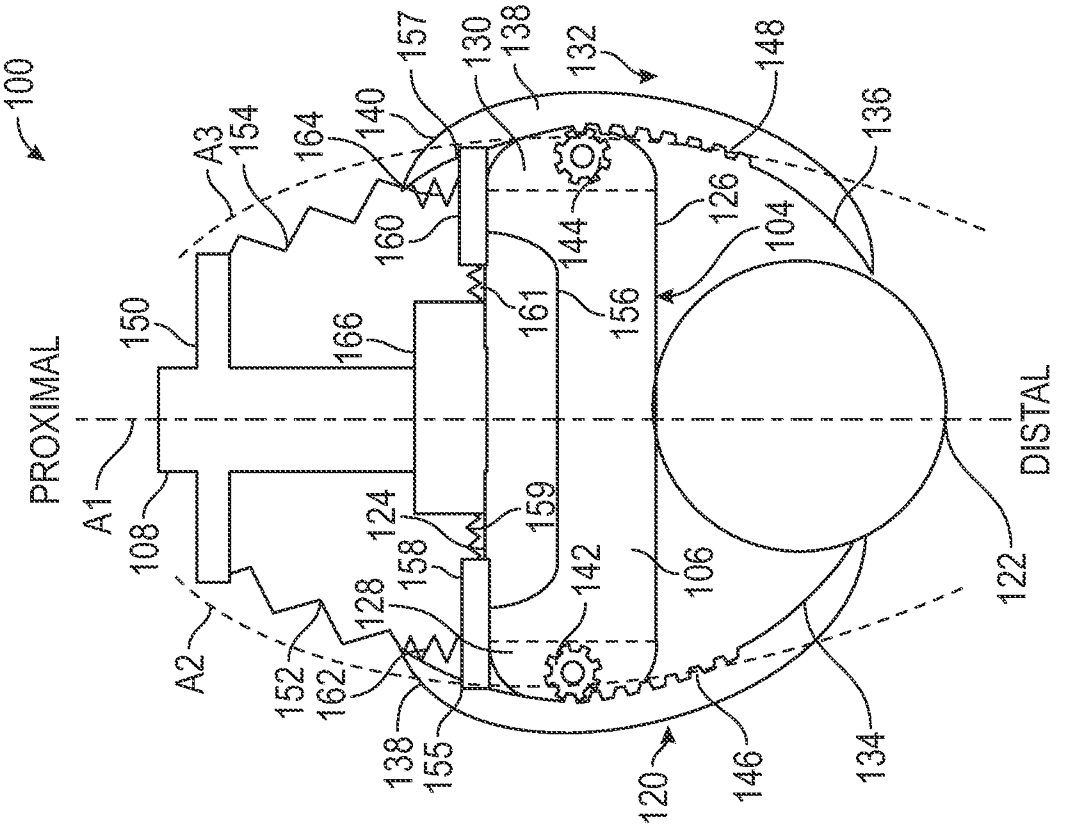
FIG. 2B illustrates a front view of the cutting guide of FIG. 2A engaging a femoral neck in a second deployed position.
Figure 2A:
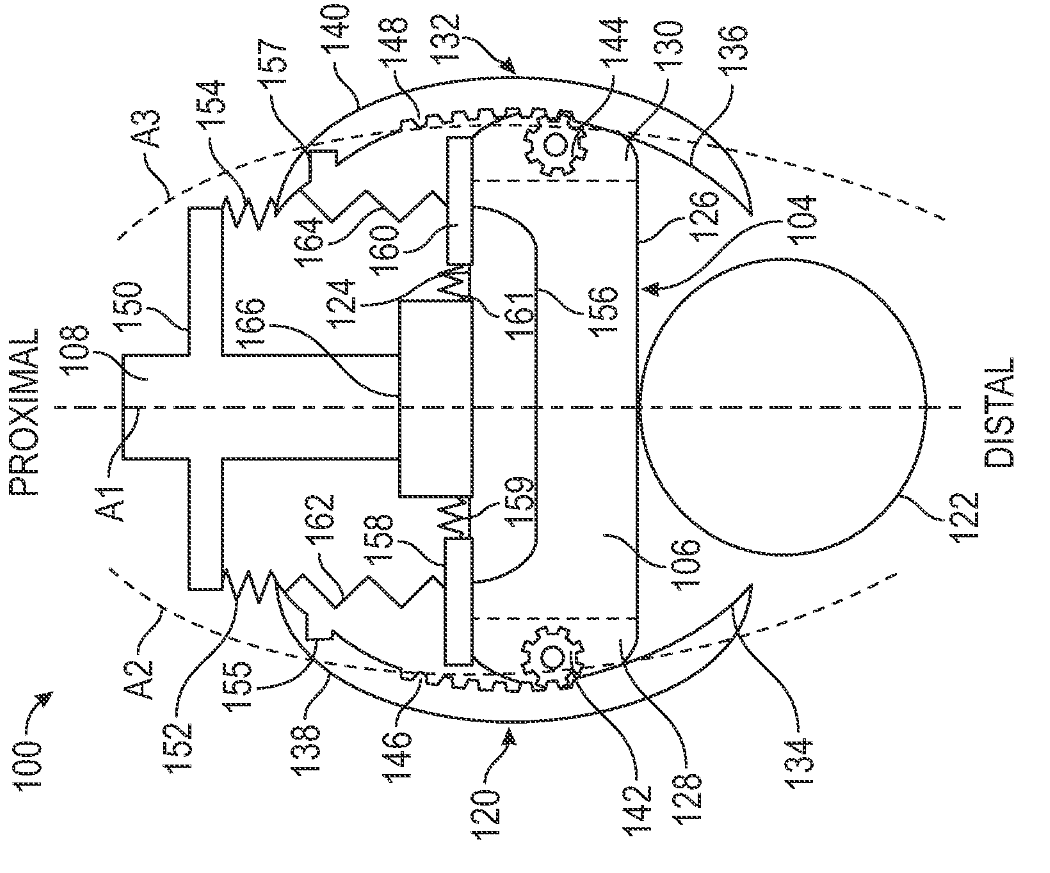
FIG. 2A illustrates front view of a cutting guide engaging a femoral neck in a first retracted position.

FIG. 2A illustrates a front view of a cutting guide 100 engaging a femoral neck 122 in a first retracted position, FIG. 2B illustrates a front view of the cutting guide 100 of FIG. 2A engaging a femoral neck 122 in a second deployed position. Also shown in FIGS. 2A-2B is a second axis A2 and a third axis A3, and orientation indicators Proximal and Distal relating to relative positions along the cutting block 104. FIGS. 2A-2B are discussed below concurrently with reference to the cutting guide 100 shown in and described with regard to FIG. 1 above. The cutting block 104 can form various three-dimensional shapes, such as including, but not limited to, ellipsoids, cuboids, triangular prisms, rectangular prisms, hexagonal prisms, octagonal prisms, or the like. The cutting block 104 can include a proximal surface 124 and distal surface 126. The proximal surface 124 and the distal surface 126 can be opposite ends or outer surfaces of the cutting block 104, such as relative to the first axis A1. For example, the proximal surface 124 and the distal surface 126 can be planar surfaces forming non-curved, curved (e.g., concave or convex), or angular shapes, or the like.

The guide surface 106 (shown in shadow in FIGS. 2A-2B) can extend along or through the cutting block 104 between the proximal surface 124 and the distal surface 126. The guide surface 106 can extend axially along or otherwise parallel to the first axis A1 (FIG. 1). The cutting block 104 can include a first shield guide surface 128 and a second shield guide surface 130. The first shield guide surface 128 and the second shield guide surface 130 can be opposite, portions, ends or segments of the cutting block 104, such as relative to the first axis A1. The first shield guide surface 128 and the second shield guide surface 130 can at least partially define, or otherwise extend along, the second axis A2 and the third axis A3, respectively. The first shield guide surface 128 and the second shield guide surface 130 can form various shapes, such as, but not limited to, non-curved, curved (e.g., concave or convex), or angular shapes, or the like.

In some examples, such as shown in FIGS. 2A-2B, the cutting guide 100 can include the first retractable shield 120 and a second retractable shield 132. In the illustrated example, the first retractable shield 120 and the second retractable shield 132 are shown partially surrounding femoral neck 122. However, in other examples, the first retractable shield 120 and the second retractable shield 132 can collectively fully surround femoral neck 122. The first retractable shield 120 and the second retractable shield 132 can form various three-dimensional shapes, such as including, but not limited to, ellipsoids, cuboids, triangular prisms, rectangular prisms, hexagonal prisms, octagonal prisms, or the like. The first retractable shield 120 and a second retractable shield 132 can be sized and shaped to conform to the femoral neck 122. For example, when the first retractable shield 120 and the second retractable shield 132 are in the second deployed position, the first retractable shield 120 and the second retractable shield can collectively contact and at least partially encircle the femoral neck 122 to secure the distal surface 126 to the femoral neck. When the femoral neck 122 is at least partially encircled by the first retractable shield 120 or the second retractable shield 132, vertical translation of a cutting instrument along the guide surface 106, such as with respect to the first axis A1, and lateral translation of a cutting instrument along the guide surface 106, such as orthogonally with respect to the first axis A1, can be limited by the first retractable shield 120 or the second retractable shield 132.

The first retractable shield 120 can include a first inner surface 134 and the second retractable shield 132 can include a second inner surface 136. The first inner surface 134 and the second inner surface 136 can generally be inner ends or segments of the first retractable shield 120 and the second retractable shield 132, respectively. For example, the first inner surface 134 can be a most medial surface of the first retractable shield 120 relative to the first axis A1, and the second inner surface 136 can be a most medial surface of the second retractable shield 132 relative to the first axis A1. The first inner surface 134 and the second inner surface 136 can be planar surfaces forming non-curved, curved (e.g., concave or convex), or angular shapes, or the like. The first inner surface 134 and the second inner surface 136 can be sized and shaped to conform to the first shield guide surface 128 or the second shield guide surface 130, respectively. For example, the first inner surface 134 and the second inner surface 136 can be concave in shape, and the first shield guide surface 128 and the second shield guide surface 130 can be convex in shape.

The first shield guide surface 128 and the second shield guide surface 130 can comprise uncovered surfaces, such as illustrated in FIGS. 2A-2B. In other examples, the first shield guide surface 128 and the second shield guide surface 130 can comprise covered surfaces that form a portion of slots or tracks extending into or through the cutting block 104 for receiving the first retractable shield 120 and the second retractable shield 132, respectively. The first retractable shield 120 can include a first outer surface 138 and the second retractable shield 132 can include a second outer surface 140. The first outer surface 138 and the second outer surface 140 can generally be outer ends or segments of the first retractable shield and the second retractable shield 132, respectively. For example, the first outer surface 138 can be a most lateral portion or surface of the first retractable shield 120 relative to the first axis A1, and the second outer surface 140 can be a most lateral portion or surface of the second retractable shield 132 relative to the first axis A1. The first outer surface 138 and the second outer surface 140 can be planar surfaces forming non-curved, curved (e.g., concave or convex), or angular shapes, or the like. The first outer surface 138 and the second outer surface 140 can be sized and shaped to be similar or different to the first inner surface 134 and the second inner surface 136, respectively. For example, the first outer surface 138 and the second outer surface 140 can be elliptically shaped, such as to facilitate sliding against soft tissue of a patient.

The first retractable shield 120 and the second retractable shield 132 can be slidable, rotatable, or otherwise movable with respect to the cutting block 104. For example, the cutting guide 100 can include a first gear 142 and a second gear 144, the first inner surface 134 can define a first plurality of teeth 146, and the second inner surface 136 can define a second plurality of teeth 148. The first gear 142 and the second gear 144 can extend laterally beyond the first shield guide surface 128 and the second shield guide surface 130 of the cutting block 104, respectively. The first gear 142 and the second gear 144 can be rotatable with respect to the cutting block 104. The first gear 142 can be configured to engage, such as by being sized and shaped, the first plurality of teeth 146. The second gear 144 can be configured to engage, such as by being sized and shaped, the second plurality of teeth 148.

In such examples, a user can apply a force to the first retractable shield 120 or the second retractable shield 132 to cause the first plurality of teeth 146 to rotate the first gear 142 or the second plurality of teeth 148 to rotate the second gear 144. The first gear 142 and the first plurality of teeth 146 can thereby collectively enable the first retractable shield 120 to be translated proximally or distally with respect to the cutting block 104, such as along the second axis A2. Similarly, the second gear 144 and the second plurality of teeth 148 can thereby collectively enable the second retractable shield 132 to be translated proximally or distally with respect to the cutting block 104, such as along third axis A3.

In other examples, the first gear 142 and the second gear 144 may not extend laterally beyond the first shield guide surface 128 and the second shield guide surface 130 of the cutting block 104, respectively. For example, the first gear 142 and the second gear 144 can be located entirely within or otherwise be encompassed by the cutting block 104. In such an example, at least a portion of the first retractable shield 120 or the second retractable shield 132 can translate proximally and distally into the cutting block 104, such as within or along tracks, grooves, bores, or other openings defined therein or therethrough configured to accommodate at least a portion of the first retractable shield 120 or the second retractable shield 132. Such tracks, grooves, bores, or other openings can be located in various positions with respect to the first axis A1, such as medial to the locations of first shield guide surface 128 and the second shield guide surface 130 illustrated in FIGS. 2A-2B. In still further examples, the first retractable shield 120 and the second retractable shield 132 can be slidable, rotatable, or otherwise movable with respect to the cutting block 104 using alternate means to the first gear 142 and the second gear 144, such as including, but not limited to, pivotable arms or levers, bushings, bearings, or the like.

The cutting guide 100 can include a projection 150. The projection 150 can generally be a protrusion or three-dimensional body extending radially or laterally outward from the arm 108. The cutting guide 100 can include a first deployment spring 152 and a second deployment spring 154. The first deployment spring 152 and the second deployment spring 154 can be configured to distally bias the first retractable shield 120 and the second retractable shield 132, respectively, such as to drive the first retractable shield 120 and the second retractable shield 132 from the first retracted position to into the second deployed position. The first deployment spring 152 and the second deployment spring 154 can be located in various positions or orientations with respect to the cutting block 104. For example, the first deployment spring 152 can extend between a portion of the first retractable shield 120, such as the first inner surface 134 or the first outer surface 138, and the projection 150. The second deployment spring 154 can extend between the second retractable shield 132, such as the second inner surface 136 or the second outer surface 140, and the projection 150. In one example, the cutting guide 100 can include only the first deployment spring 152 and the first retractable shield 120.

The cutting guide 100 can include a lock system 156. The lock system 156 can be configured to maintain the first retractable shield 120 or the second retractable shield 132 in the first retracted position or in the second deployed position. For example, the lock system 156 can include, for example, but not limited to, a first lock 158 and a second lock 160. The first lock 158 and the second lock 160 can be located in various positions on, or with respect to, the cutting block 104 or the arm 108. For example, the first lock 158 can be translatable along the proximal surface 124 of the cutting block 104, such as to engage or disengage the first inner surface 134 of the first retractable shield 120 to prevent translation of the first retractable shield 120 along the second axis A2. Similarly, the second lock 160 can be translatable along the proximal surface 124 of the cutting block 104, such as to engage or disengage the second inner surface 136 of the second retractable shield 132 to prevent translation of the second retractable shield 132 along the third axis A3.

In some examples, the first retractable shield 120 or the second retractable shield 132 can include a first recess 155 and a second recess 157. The first recess 155 and the second recess 157 can be configured to receive or otherwise retain a portion of the first lock 158 and the second lock 160, respectively. The first recess 155 and the second recess 157 can extend through the first inner surface 134 and the second inner surface 136, respectively, in various positions or orientations relative to the cutting block 104. For example, as illustrated in FIGS. 2A-2B, the first recess 155 and the second recess 157 can be defined in a generally upper or proximal portion of the first retractable shield 120 and the second retractable shield 132, respectively, such as to enable a user to translate the first lock 158 or the second lock 160 laterally along the proximal surface 124 of the cutting block 104 into the first recess 155 and the second recess 157, respectively, to secure the first retractable shield 120 and the second retractable shield 132 in the second deployed position or the first retracted position. In one example, the cutting guide 100 can include only the first lock 158 and the first recess 155.

In some examples, the lock system 156 can include a first lock spring 159 and a second lock spring 161. The first lock spring 159 and the second lock spring 161 can be configured to laterally bias the first lock 158 and the second lock 160, respectively, toward the first retractable shield 120 and the second retractable shield 132, respectively. For example, the first lock spring 159 or the second lock spring 161 can drive the first lock 158 or the second lock 160, respectively, into the first recess 155 or the second recess 157 when the first retractable shield 120 or the second retractable shield 132 is in the second deployed position. The first lock spring 159 and the second lock spring 161 can be located in various positions or orientations with respect to the cutting block 104. For example, the first lock spring 159 can extend between the first lock 158 and a portion of the arm 108 or a motor 166. The second lock spring 161 can extend between the second lock 160 and a portion of the arm 108 or the motor 166. In one example, the cutting guide 100 can include only the first lock spring 159 and the first lock 158.

In some examples, the cutting guide 100 can include a first retraction spring 162 and a second retraction spring 164 (FIG. 2A). The first retraction spring 162 and the second retraction spring 164 can be configured to proximally bias the first retractable shield 120 and the second retractable shield 132, respectively, such as to drive the first retractable shield 120 and the second retractable shield 132 from the second deployed position into the first retracted position. The first retraction spring 162 and the second retraction spring 164 can be located in various positions or orientations with respect to the cutting block 104. For example, the first retraction spring 162 can extend between a portion of the first retractable shield 120, such as the first inner surface 134 or the first outer surface 138, and the first lock 158. The second retraction spring 164 can extend between the second retractable shield 132, such as the second inner surface 136 or the second outer surface 140, and the second lock 160.

In one example, the cutting guide 100 can include only the first retraction spring 162 and the first retractable shield 120. In some examples, the cutting guide 100 can include only one of the first lock spring 159, the second lock spring 161, the first deployment spring 152, the second deployment spring 154, the first retraction spring 162, and the second retraction spring 164. Any of the first lock spring 159, the second lock spring 161, the first deployment spring 152, the second deployment spring 154, the first retraction spring 162, and the second retraction spring 164 can be, for example, but not limited to, a coil spring, a wave spring, a leaf spring, or the like.

In some examples, the cutting guide 100 can include the motor 166, such as alternatively to the first deployment spring 152, the second deployment spring 154, the first retraction spring 162, or the second retraction spring 164. The motor 166 can be, for example, but not limited to, an electric or pneumatic motor. The motor 166 can be connected to the robotic surgical system 102 (FIG. 1) such that the motor 166 can receive power therefrom. The motor 166 can be configured to drive the first retractable shield 120 proximally or distally along the second axis A2 and the second retractable shield 132 proximally or distally along the third axis A3, such as via a user input to the motor 166. The motor 166 can additionally be configured to activate the first lock 158 and the second lock 160. For example, the motor 166 can be connected to the first gear 142 and the second gear 144, such as to rotate the first gear 142 and the second gear 144 to thereby drive the first retractable shield 120 or the second retractable shield 132 via rotatable engagement between the first gear 142 and the second gear 144 and the first plurality of teeth 146 and the second plurality of teeth 148, respectively.

Figure 3B:
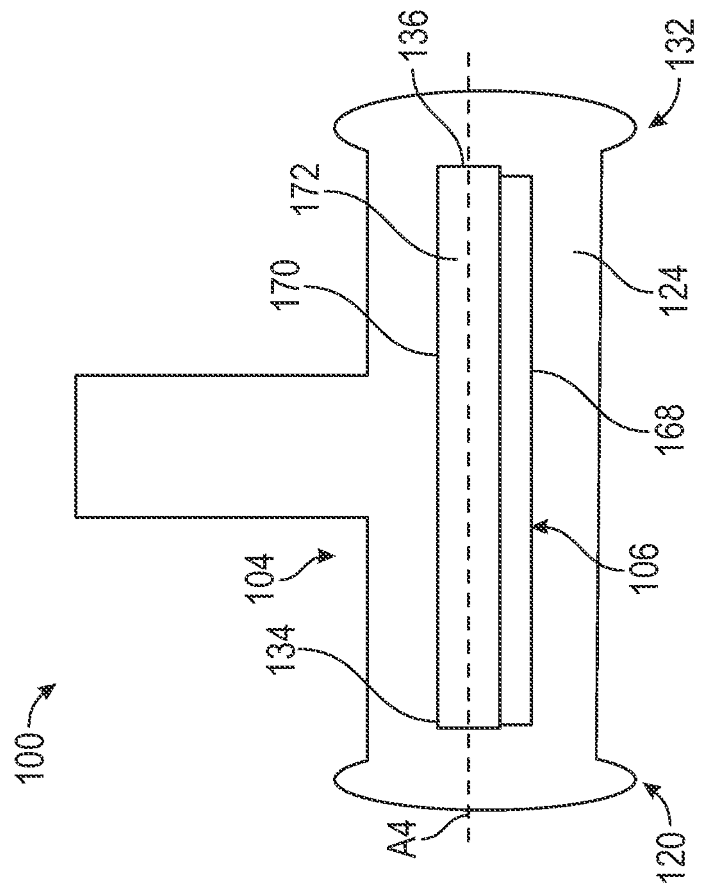
FIG. 3B illustrates a top view of the cutting guide of FIG. 3A including a door.
Figure 3A:
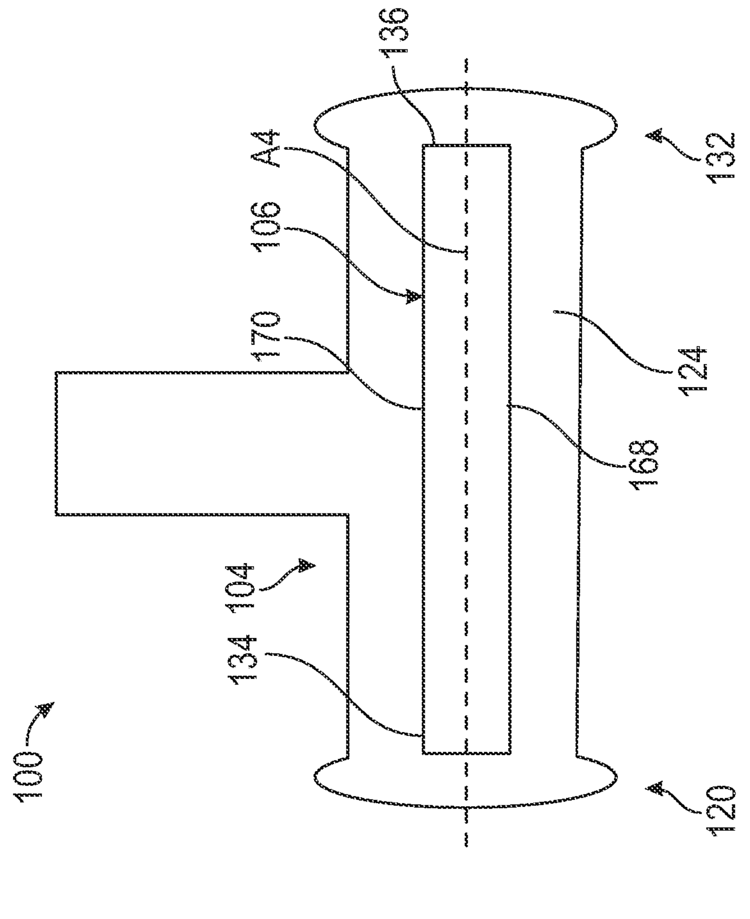
FIG. 3A illustrates a top view of a cutting guide.

FIG. 3A illustrates a top view of a cutting guide 100. FIG. 3B illustrates a top view of the cutting guide 100 of FIG. 3A including a door 172. Also shown in FIGS. 3A-3B is a fourth axis A4. FIGS. 3A-3B are discussed below concurrently with reference to the cutting guide 100 shown in and described with regard to FIGS. 1-2B above and certain features are omitted for clarity. As shown in FIGS. 3A-3B, the guide surface 106 can be a slot, a rectangular bore, or otherwise a bounded opening extending longitudinally through the cutting block 104 between the proximal surface 124 and the distal surface 126 (FIGS. 2A-2B). As discussed with reference to FIGS. 4A and 4B, the cutting surfaces of the present disclosure can be unbounded.

In such an example, the guide surface 106 can include a first surface 168 and a second surface 170. Either of the first surface 168 or the second surface 170 can be configured to resist contact by a rotating or reciprocating cutting blade of a cutting instrument to guide the cutting blade along a resection trajectory. The guide surface 106 can extend at least partially between the first shield guide surface 128 (FIGS. 2A-2B) and the second shield guide surface 130

(FIGS. 2A-2B) of the cutting block 104. For example, the guide surface 106 can extend laterally between the first inner surface 134 of the first retractable shield 120 and the second inner surface 136 of the second retractable shield 132 along the fourth axis A4, such as to thereby limit lateral translation of a cutting instrument along the guide surface 106 to protect soft tissue of a patient located proximally to the femoral neck 122 (FIGS. 2A-2B).

As shown in FIG. 3B, the cutting guide 100 can include the door 172. The door 172 can be configured to inhibit access to the guide surface 106. For example, the door 172 can be sized and shaped to fully obstruct or at least partially cover the guide surface 106. The door 172 can form various three-dimensional shapes, such as including, but not limited to, ellipsoids, cuboids, triangular prisms, rectangular prisms, hexagonal prisms, octagonal prisms, or the like. The door 172 can be configured to be slidable, rotatable, or otherwise movable with respect to the cutting block 104 using various means, such as including, but not limited to, a gear, a pivotable arm or lever, a bushing, a bearing, or the like. For example, the door 172 can be slidable along the fourth axis A4 or first axis A1 (FIGS. 1-2B). In some examples, the door 172 can be slidable along the first axis A1 in the proximal-distal direction and can be partially or fully concealed within the body of cutting block 104, as shown in FIG. 3A. The door 172 can further be operably connected to the first retractable shield 120, the second retractable shield 132, the first lock 158 (FIGS. 2A-2B), or the second lock 160 (FIGS. 2A-2B). For example, translation or operation of any of the first retractable shield 120, the second retractable shield 132, the first lock 158, or the second lock 160 can cause the door 172 to move with respect to the guide surface 106.

In various such examples, when the first retractable shield 120 or the second retractable shield 132 are in the first retracted position, the door 172 can be located over the guide surface 106, and when the first retractable shield 120 or the second retractable shield 132 is in the second deployed position, the door 172 can be offset from the guide surface 106. For example, the door 172 can be coupled to the first inner surface 134 of the first retractable shield 120 or the first outer surface 138 of the second retractable shield 132, such as to enable distal translation of the first retractable shield 120 to cause the door 172 to translate along the proximal surface 124 of the cutting block 104 away from the guide surface 106. The door 172 can thereby prevent a user from engaging the guide surface 106 until the first retractable shield 120 or the second retractable shield 132 is in the second deployed position.

The cutting guide 100, including any of various components thereof shown in and described above with regard to FIGS. 1-3B, such as the cutting block 104, the arm 108 (FIG. 1), the first retractable shield 120, the second retractable shield 132, the first gear 142, or the second gear 144, the first plurality of teeth 146, or the second plurality of teeth 148, can be made from, but not limited to, plastics, composites, rubber, or ceramics. For example, the components listed above can be molded, printed, or otherwise made from, ABS plastic. In other examples, the cutting guide 100, including any of various components thereof shown in and described above with regard to FIGS. 1-3B, such as the such as the cutting block 104, the arm 108 (FIG. 1), the first retractable shield 120, the second retractable shield 132, the first gear 142, or the second gear 144, the first plurality of teeth 146, or the second plurality of teeth 148, can be made from, but not limited to, stainless steel, aluminum, or other metals, such as via machining or metallic molding. The materials can be selected so as to be stronger than the force applied by a cutting instrument to prevent such instrument from cutting through the components. In other examples, the materials can be selected to provide feedback to the user or the surgeon that the cutting instrument has passed through the femoral neck.

Figure 4B:
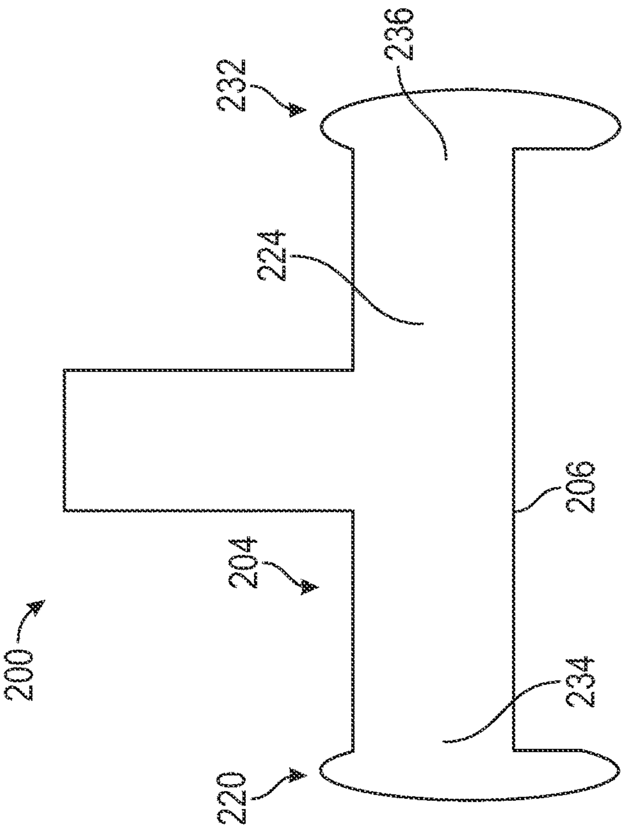
FIG. 4B illustrates a top view of the cutting guide of FIG. 4A.
Figure 4A:
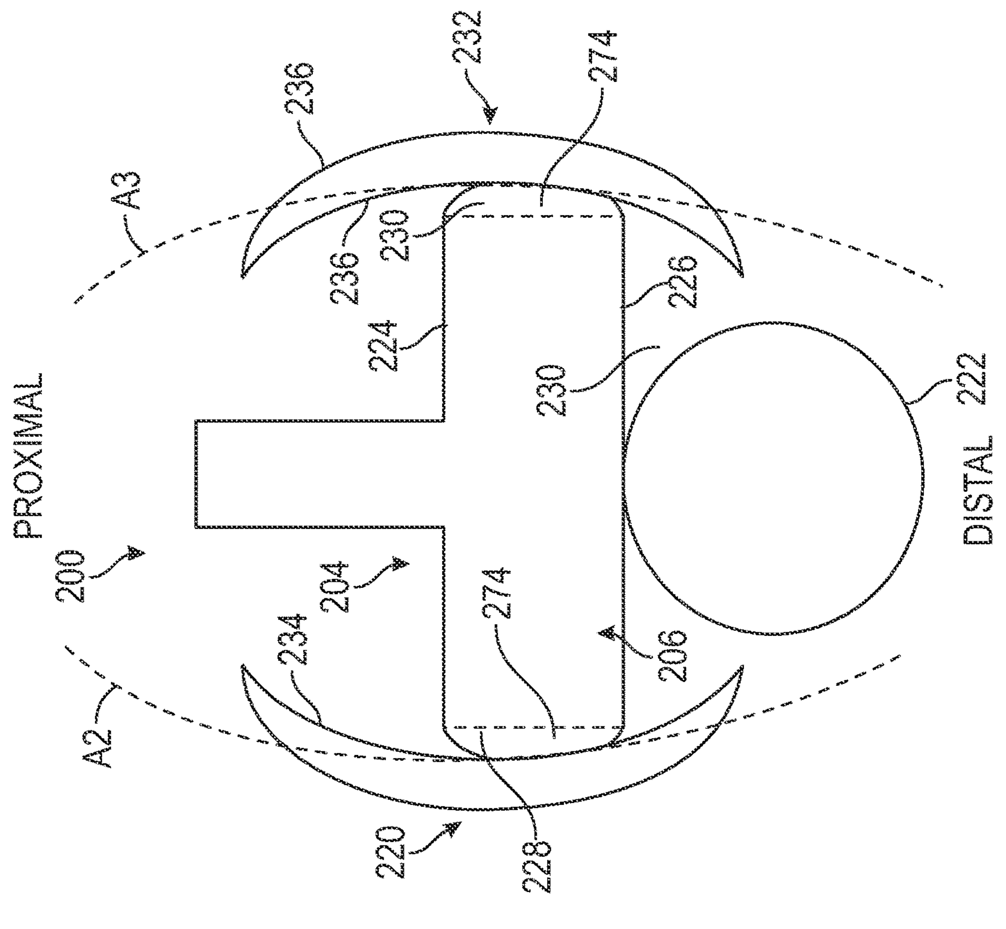
FIG. 4A illustrates front view of a cutting guide in a first retracted position.

FIG. 4A illustrates a front view of a cutting guide 200 in a first retracted position. FIG. 4B illustrates a top view of the cutting guide 200 of FIG. 4A. Also shown in FIG. 4A is second axis A2 and a third axis A3, and orientation indicators Proximal and Distal relating to relative positions along the cutting guide 200. The cutting guide 200 can be similar to the cutting guide 100 shown in and discussed with regard to FIGS. 1-3B above, at least in that the cutting guide 200 can include a cutting block 204, a guide surface 206, a first retractable shield 220, and a second retractable shield 232.

As shown in FIG. 4B, the guide surface 206 can be extend longitudinally through the cutting block 204 between the proximal surface 224 and the distal surface 226. The guide surface 206 can generally be an unbounded surface or recess laterally offset from an front surface 274 of the cutting block 204, such as including the first end surface 228 or the second end surface 230. For example, the guide surface 206 can extend laterally between the first inner surface 234 of the first retractable shield 120 and the second inner surface 236 of the second retractable shield 232, such as to thereby limit lateral translation of a cutting instrument along the guide surface 206 to protect soft tissue of a patient located proximally to the femoral neck 222. The guide surface 206 can enable a user to engage the guide surface 206 with a cutting instrument from an additional or third direction, such as relative to the guide surface 106 shown in FIGS. 2A-3B.

Figure 5:
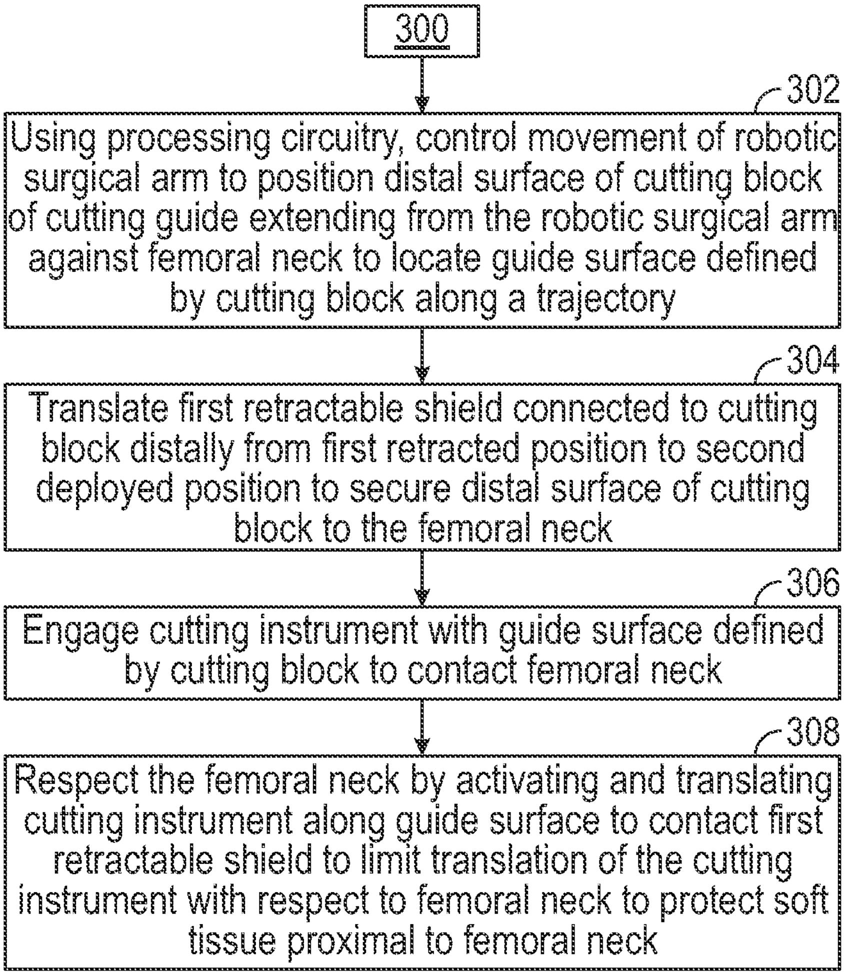
FIG. 5 illustrates a method of resecting a femoral neck during a robotically assisted hip replacement procedure.

FIG. 5 illustrates a method 300 of resecting a femoral neck during a robotically assisted hip replacement procedure. The steps or operations of the method 300 are illustrated in a particular order for convenience and clarity; many of the discussed operations can be performed by multiple different actors, devices, or systems. It is understood that subsets of the operations discussed in the method 300 can be attributable to a single actor, device, or system and can be considered a separate standalone process or method.

The method can include operation 302. The operation 302 can include using processing circuitry, controlling movement of a robotic surgical arm to position a distal surface of a cutting block of a cutting guide extending from the robotic surgical arm against or in close proximity to the femoral neck 122 to locate a guide surface defined by the cutting block along a trajectory. For example, a user can control the robotic surgical arm using a control system, such as to position the cutting guide on or with respect to a femoral head or neck of a patient, within an access incision. The robotic surgical arm can additionally be automatically moved by moving the robotic arm into a known configuration in a three-dimensional coordinate system using a surgical tracking system, as described below.

The method 300 can include operation 304. The operation 304 can include translating a first retractable shield connected to the cutting block distally from a first retracted position to a second deployed position to secure the distal surface of the cutting block to the femoral neck. For example, a user can manually apply a force to the first retractable shield or the second retractable shield to cause the first retractable shield or the second retractable shield to translate in a distal direction relative to the cutting block. In some examples, a user can translate the first retractable shield or a second retractable shield using processing circuitry of the robotic surgical arm to cause the first retractable shield to translate distally via electric or pneumatic assistance, such as provided by an electric or pneumatic motor connected to the first or a second retractable shield.

In some examples, a user can translate the first retractable shield or a second retractable shield operating a lock to cause the first retractable shield to translate distally under spring pressure. For example, a user can translate a first or a second lock positioned on the cutting block to disengage the first retractable shield or a second retractable shield, respectively, such as to allow a deployment spring to drive the first retractable shield or the second retractable shield distally into the second deployment position from the first retracted position.

In still further examples, translating the first retractable shield can further include translating a door inhibiting engagement of the cutting instrument with the guide surface when the first retractable shield is in the first retracted position to translate with respect to the guide surface to enable engagement of the cutting instrument with respect to the guide surface when the first shield retractable shield is in the second deployed position. For example, the door can be connected to a first inner surface or a first outer surface of the first retractable shield to enable distal translation of the first retractable shield to cause the door to translate along the cutting block away from the guide surface of the cutting block.

The method 300 can include operation 306. The operation 306 can include engaging a cutting instrument with the guide surface defined by the cutting block to contact the femoral neck. For example, a user can insert into or otherwise contact the guide surface of the cutting block with a blade of the cutting instrument to position the blade of the cutting instrument with respect to the femoral neck.

The method 300 can include operation 306. The operation 308 can include resecting the femoral neck by activating and translating the cutting instrument along the guide surface to contact the first retractable shield to limit translation of the cutting instrument with respect to the femoral neck to protect soft tissue proximal to the femoral neck. For example, a user can translate a rotating or reciprocating cutting blade of the cutting instrument laterally or vertical along the guide surface until the cutting blade contacts an inner surface of the first retractable shield or a second inner surface of a second retractable shield. Thus, the shields can prevent undesirable cutting of soft tissue located distally of the femoral neck.

Figure 6:
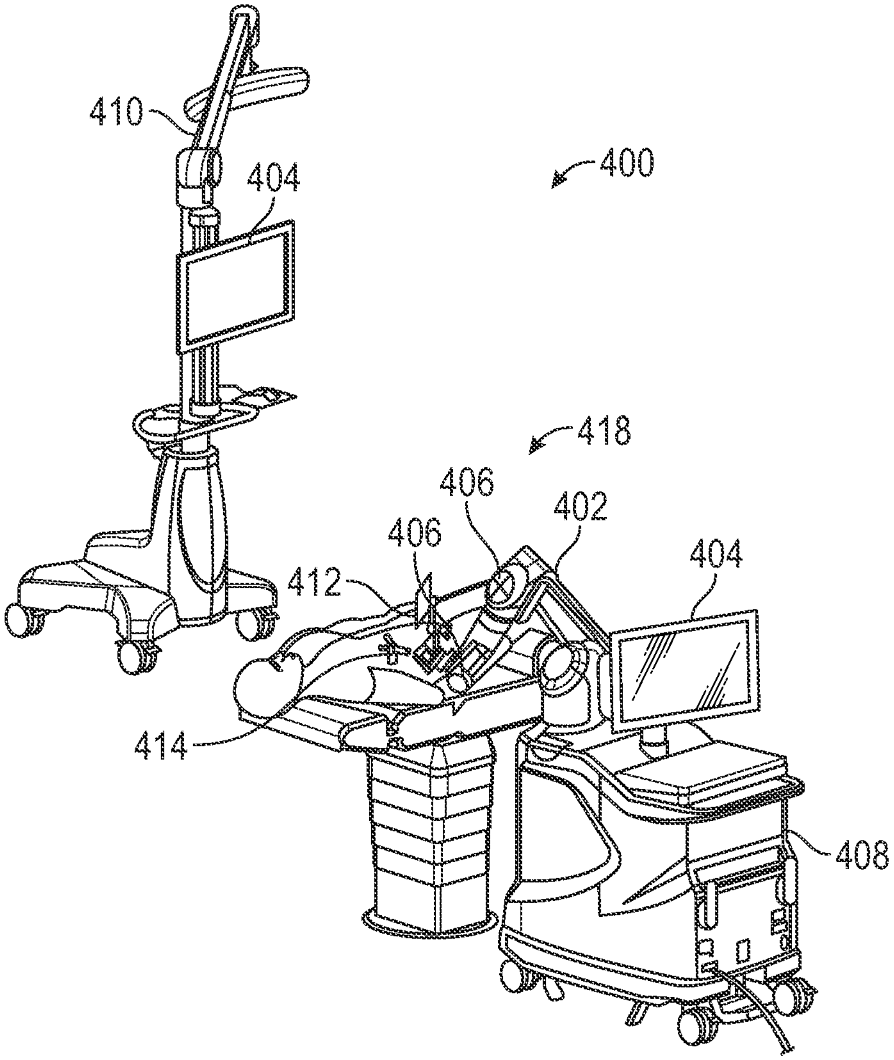
FIG. 6 illustrates a perspective view of a robotic surgical system.

FIG. 6 illustrates a robotic surgical system 400. FIG. 6 is discussed with reference to the cutting guide 100 and the robotic surgical system 102 shown in and described with regard to FIGS. 1-3B above. The robotic surgical system 400 can include the robotic surgical arm 402. The robotic surgical arm 402 can be similar to the robotic surgical arm 418 shown in and discussed with regard to FIG. 1 above. The robotic surgical arm 402 can be controlled by a surgeon with various control devices or systems. For example, a surgeon can use a control system (e.g., a controller that is processor-implemented based on machine-readable instructions, which when implemented cause the robotic arm to move automatically or to provide force assistance to surgeon-guided movement) to guide the robotic surgical arm 402. A surgeon can use anatomical imaging, such as displayed on display screens 404, to guide and position the robotic surgical arm 402.

Anatomical imaging can be provided to the display screens 404 with various imaging sources, such as one or more cameras positioned on the robotic surgical arm 402, or intraoperative fluoroscopy, such as a C-arm. The robotic surgical arm 402 can include two or more articulating joints 406 capable of pivoting, rotating, or both, to provide a surgeon with wide range of adjustment options. The anatomical imaging, for example, can be imaging of internal patient anatomy within an incision. Such an incision can be made in a variety of positions on a patient. For example, in a hip arthroplasty procedure, the incision can be made in a hip region of a patient, such as to allow the cutting guide 100, when coupled to the robotic surgical arm 402, to access a bone surface or other anatomy of the patient.

The robotic surgical arm 402 can include a computing system 408, which can also communicate with the display screens 404 and a tracking system 410. The tracking system 410 can be operated by the computing system 408 as a stand-alone unit. The computing system 408 can utilize the Polaris optical tracking system from Northern Digital, Inc. of Waterloo, Ontario, Canada. Additionally, the tracking system 410 can comprise the tracking system shown and described in Pub. No. US 2017/0312035, titled "Surgical System Having Assisted Navigation" to Brian M. May, which is hereby incorporated by this reference in its entirety. The tracking system 410 can monitor a plurality of tracking elements, such as tracking elements 412 and 414. The tracking elements 412 and 414 can be affixed to objects of interest, to track locations of multiple objects within a surgical field.

The tracking system 410 can function to create a virtual three-dimensional coordinate system within the surgical field for tracking patient anatomy, surgical instruments, or portions of the robotic surgical arm 402 such as including the cutting guide 100 when connected thereto. One or more of the tracking elements 412 and 414 can be tracking frames including multiple IR reflective tracking spheres, or similar optically tracked marker devices. In an example, one or more of the tracking elements 412 and 414 can be placed on or adjacent one or more bones of patient. In other examples, one or more of the tracking elements 412 and 414 can be placed on the cutting guide 100 or on an implant to accurately track positions within the virtual coordinate system. In each instance, the tracking elements 412 and 414 can provide position data, such as a patient position, a bone position, a joint position, an implant position, a position of the robotic surgical arm 402, or the like.

In the operation of some examples, the cutting guide 100 can be connected to the robotic surgical arm 402 in preparation for a surgical arthroplasty procedure. The surgical procedure can be a total hip arthroplasty; but can also be other types of joint replacement procedures. A surgeon can then make an incision in a hip region of a patient. The robotic surgical arm 402 can guide and position the cutting block 104 (FIG. 1) within the incision. For example, the cutting guide 100 can be guided to a femoral neck of a patient using the robotic surgical arm 402 in a cooperatively-controlled mode utilizing robotic guidance, such as to position the guide surface 106 (FIGS. 1-3B) proximal to the femoral neck in alignment with a resection trajectory. The first retractable shield 120 of the second retractable shield 132 can then be translated distally by the surgeon to concurrently engage the femoral neck and prevent a cutting instrument positioned along or otherwise engaged with the cutting block to contact soft tissue of the patient located proximal to the femoral neck. In one example, the surgeon can use the computing system 408 of the robotic surgical system 400 to electrically or pneumatically drive or otherwise translate a first retractable shield (FIGS. 1-3B), or second retractable shield (FIGS. 2-3B), via an electrical or pneumatic motor.

The cutting guide 100 and the robotic surgical system 400 can thereby improve femoral neck resection of a patient. In contrast to methods utilizing a traditional cutting guide and manual positioning thereof, the operation of the cutting guide 100, such as including positioning a cutting guide to 100 to set an angle or trajectory of the cutting guide, securing the cutting guide to a bone surface, or limiting or preventing contact of a cutting instrument engaged therewith with soft tissues of a patient, can be more easily carried out using the cutting guide 100. Further, the ability of the robotic surgical arm 402 to be adjustably pivoted, rotated, or otherwise articulated intra-procedurally, either autonomously or cooperatively with the operator, can help to increase the precision and reduce the duration of an arthroplasty procedure. For example, the robotic surgical arm 402 can control the position and movement of the cutting guide 100 more precisely and steadily than a human hand. These benefits can enable a surgeon to complete a hip arthroplasty with improved accuracy and less fatigue; and provide a patient with shorter hospital stay and a reduced recovery time.

Figure 7:
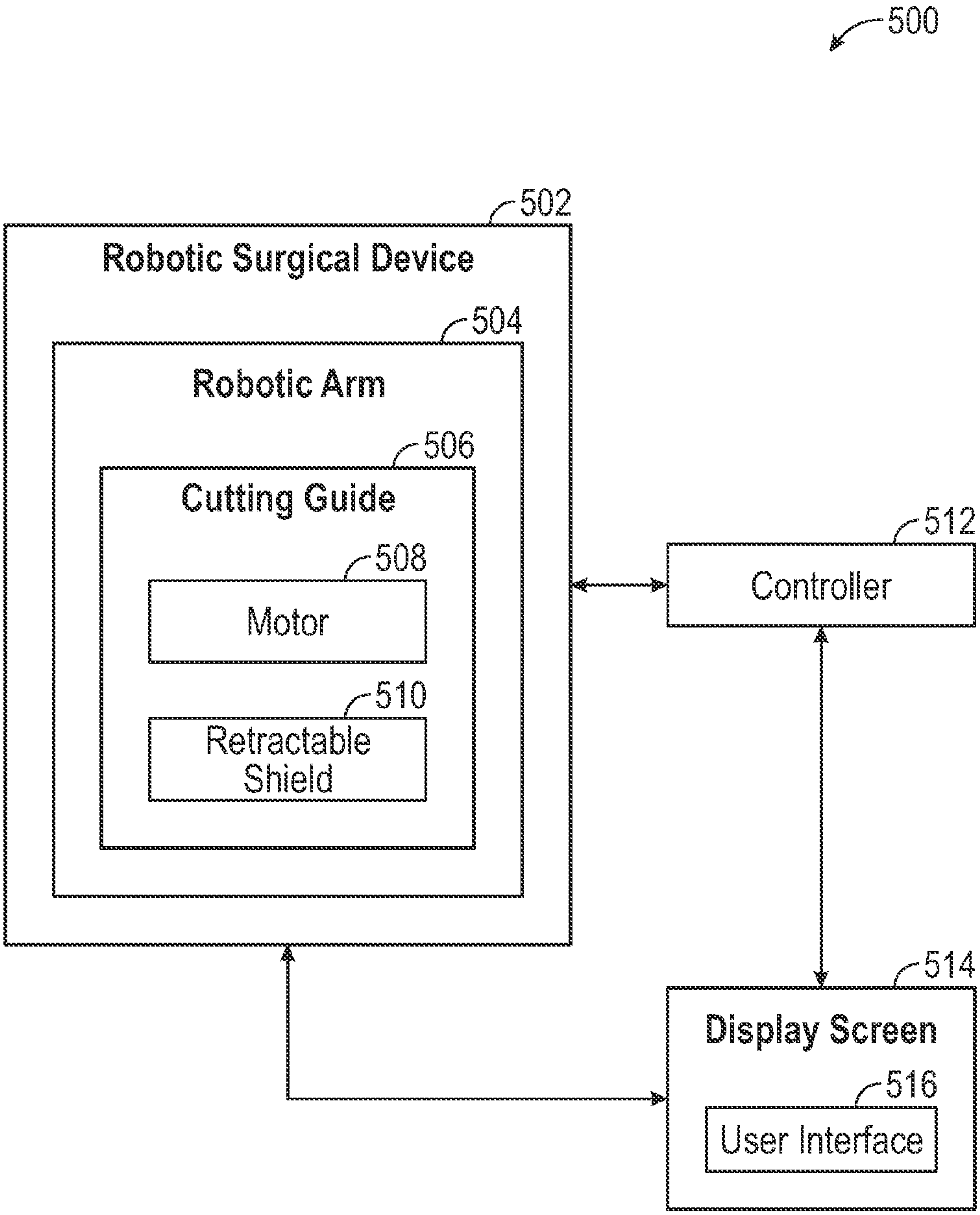
FIG. 7 illustrates a schematic view of a robotic surgical system for robotically assisted femoral resection.

FIG. 7 illustrates a schematic view of a robotic surgical system 500 for robotically assisted femoral resection. The robotic surgical system 500 includes a robotic surgical device 502, which can include a robotic surgical arm 504, and a cutting guide 506. The cutting guide 506 can include a motor 508 and a retractable shield 510. The robotic surgical arm 504 can be similar to the robotic surgical arm 118 discussed above with respect to FIG. 1, at least in that robotic surgical arm 504 can be a movable and articulatable robotic arm. The cutting guide 506 can be similar to the cutting guide 100 or cutting guide 200 shown in and discussed with respect to FIGS. 1-3B or FIGS. 4A-4B, respectively, above.

The robotic surgical arm 504 can move autonomously in an example. In another example, the robotic surgical arm 504 can provide a force assist to surgeon or user guided movements. In yet another example, a combination of autonomous movement and force assist movement can be performed by the robotic surgical arm 504 (e.g., force assist for an initial movement, and autonomously moving a later movement). In an example, the robotic surgical arm 504 can resist an applied force. For example, the robotic surgical arm 504 can be programmed to stay within a particular range of locations or a particular position, move at a particular speed (e.g., resist a higher speed by resisting force), or the like.

The robotic surgical device 502 can output or receive data from a controller 512. The controller 512 can be implemented in processing circuitry (e.g., hardwired or a processor), a programmable controller, such as a single or multi-board computer, a direct digital controller (DDC), a programmable logic controller (PLC), a system on a chip, a mobile device (e.g., cell phone or tablet), a computer, or the like. In one example, the controller 512 can output information to a display screen 514. The display screen 514 can retrieve and display information from an imaging camera. The imaging camera can be physically positioned on the robotic surgical device 502, such as on the robotic surgical arm 504 or on the cutting guide 506.

In an example, the display screen 514 can be used to display a user interface 516. In an example, the display screen 514 can be a touch screen display. In another example, the user interface 516 on the display screen 514 can provide lights, buttons, or switches. A user can thereby interact with the display screen 514 and the user interface 516 to input control commands, which can be relayed to the robotic surgical device 502 through the controller 512 to control the robotic surgical device 502. In one example, a user can use the display screen 514 to view or otherwise monitor a position of a first retractable shield (FIGS. 1-3B) or second retractable shield (FIGS. 2-3B), such as to ensure that soft tissue of a patient is adequately protected. The robotic surgical system 500 can be used to perform all, or a portion of, a surgical procedure on a patient.

In the operation of some examples, a user can interact with the user interface 516 on the display screen 514 to power on the robotic surgical device 502. Power can be indicated by a light, for example, on the user interface 516, or on the robotic surgical arm 504. When the robotic surgical device 502 is powered on, the user can operate the robotic surgical arm 504 by interacting with the display screen 514 and the user interface 516. In other examples, cutting guide 506 can be operated separately from the robotic surgical arm 504, such as by manually translating or otherwise operating aspects of or features of the cutting guide 506, such as the retractable shield 510 or the motor 508.

The robotic surgical system 500 can be used to resect or otherwise cut a bone surface of a patient, such as the femoral neck 122 (FIGS. 2A-3B) along a resection trajectory, by translating a cutting instrument along the cutting guide 506. In an example, the resection trajectory or cutting angle defined by the cutting guide 506 can be changed intra-operatively, for example, by using the controller 512. The robotic surgical arm 504 can thereby allow a user to respond to specific bone conditions of a patient, such as to improve an amount of a patient's bone that can be preserved during an arthroplasty procedure by increasing the consistency and precision of impaction of the bone surface. The bone penetration depth and the maximum lateral positioning of a cutting instrument engaged with the cutting guide can further be precisely controlled or otherwise limited using the robotic surgical arm 504 and the cutting guide 506, in contrast to traditional manually guided or hand-held cutting guides.

Figure 8:
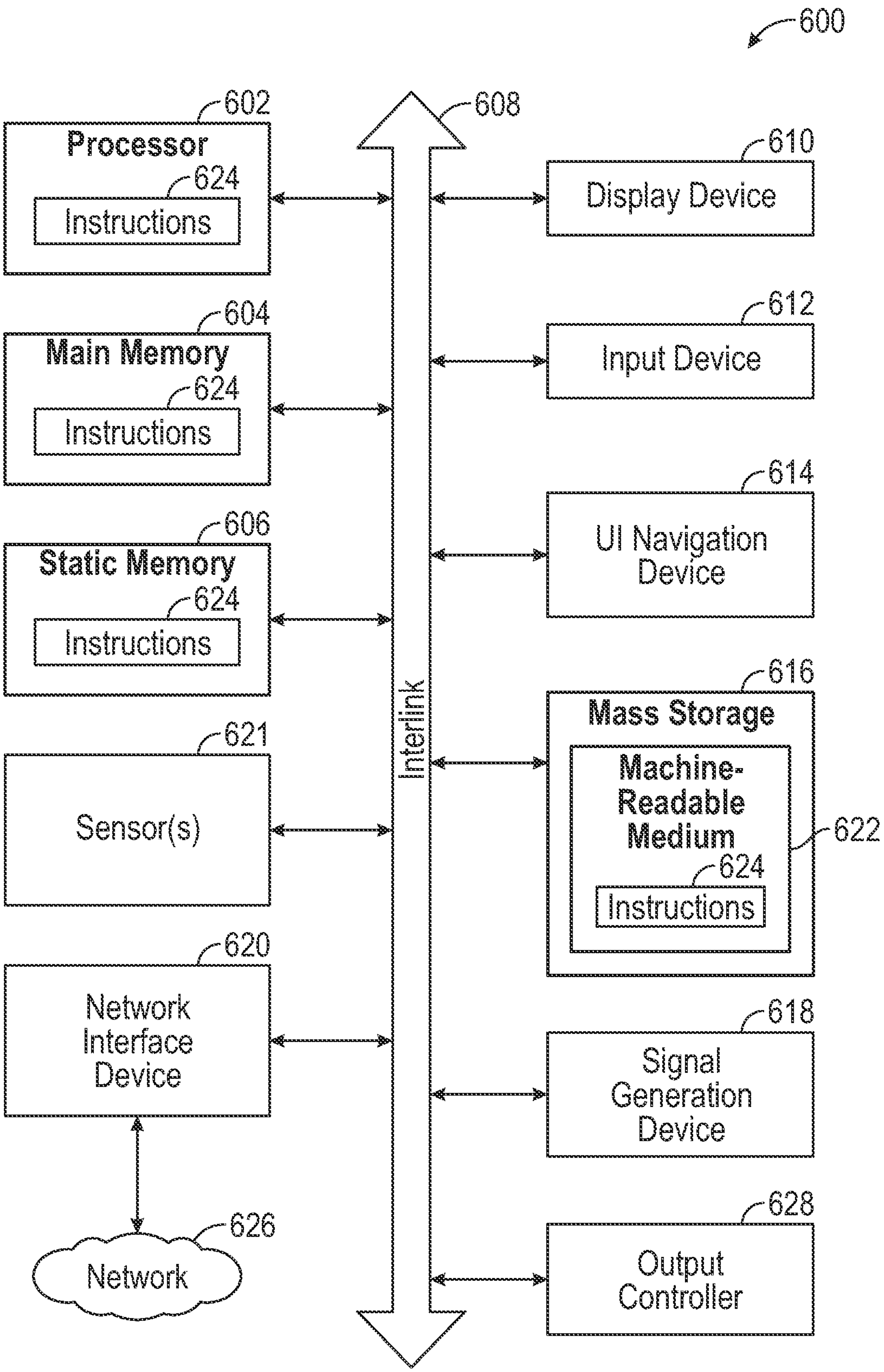
FIG. 8 illustrates a block diagram of an example machine upon which any one or more of the techniques discussed herein can be performed.

FIG. 8 illustrates a block diagram of an example machine 600 upon which any one or more of the techniques discussed herein can be performed. In alternative embodiments, the machine 600 can operate as a standalone device or can be connected (e.g., networked) to other machines. In a networked deployment, the machine 600 can operate in the capacity of a server machine, a client machine, or both in server-client network environments. In an example, the machine 600 can act as a peer machine in peer-to-peer (P2P) (or other distributed) network environment.

The machine 600 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations. In examples, machine 600 can be configured to coordinate operation of the robotic surgical system 400 (FIG. 6) and the cutting guide 100 (FIGS. 1-3B) such as by positioning the cutting block 104 in a location where the first retractable shield 120 and the second retractable shield 132 can protect soft tissue, and, to automatically deploy upon a user input, the first retractable shield 120 or the second retractable shield 132, as well as other locking or blocking devices, such as the first lock 158 (FIGS. 2A-2B) or the second lock 160 (FIGS. 2A-2B).

Machine (e.g., computer system) 600 can include a hardware processor 602 (e.g., a central processing unit (CPU), a graphics processing unit (GPU), a hardware processor core, or any combination thereof), a main memory 604 and a static memory 606, some or all of which can communicate with each other via an interlink (e.g., bus) 608. The machine 600 can further include a display unit 610, an alphanumeric input device 612 (e.g., a keyboard), and a user interface (UI) navigation device 614 (e.g., a mouse). In an example, the display unit 610, alphanumeric input device 612 and UI navigation device 614 can be a touch screen display. The machine 600 can additionally include a storage device (e.g., drive unit) 616, a signal generation device 618 (e.g., a speaker), a network interface device 620, and one or more sensors 621, such as a global positioning system (GPS) sensor, compass, accelerometer, or other sensors. The machine 600 can include an output controller 628, such as a serial (e.g., Universal Serial Bus (USB), parallel, or other wired or wireless (e.g., infrared (IR), near field communication (NEC), etc.) connection to communicate or control one or more peripheral devices (e.g., a printer, card reader, etc.).

The storage device 616 can include a machine readable medium 622 on which is stored one or more sets of data structures or instructions 624 (e.g., software) embodying or utilized by any one or more of the techniques or functions described herein, such as the method 300 of FIG. 5 and the associated operations discussed. The instructions 624 can also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 can constitute machine readable media.

While the machine readable medium 622 is illustrated as a single medium, the term "machine readable medium" can include a single medium or multiple media (e.g., a centralized or distributed database, or associated caches and servers) configured to store the one or more instructions 624. The term "machine readable medium" can include any medium that is capable of storing, encoding, or carrying instructions for execution by the machine 600 and that cause the machine 600 to perform any one or more of the operations or techniques of the present disclosure discussed above, or that is capable of storing, encoding or carrying data structures used by or associated with such instructions. Non-limiting machine readable medium examples can include solid-state memories, and optical and magnetic media.

The instructions 624 can further be transmitted or received over a communications network 626 using a transmission medium via the network interface device 620 utilizing any one of a number of transfer protocols (e.g., frame relay, internet protocol (IP), transmission control protocol (TCP), user datagram protocol (VIP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 822.16 family of standards known as WiMax®), IEEE 802.15.4 family of standards, peer-to-peer (P2P) networks, among others.

In an example, the network interface device 620 can include one or more physical jacks (e.g., Ethernet, coaxial, or phone jacks) or one or more antennas to connect to the communications network 626. In an example, the network interface device 620 can include a plurality of antennas to wirelessly communicate using at least one of single-input multiple-output (SIMO), multiple-input multiple-output (MTMO), multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

The above description and the drawings sufficiently illustrate specific examples to enable those skilled in the art to practice them. Other examples may incorporate structural, process, or other changes. Portions and features of some examples may be included in, or substituted for, those of other examples. Examples set forth in the claims encompass all available equivalents of those claims.

The foregoing systems and devices, etc. are merely illustrative of the components, interconnections, communications, functions, etc. that can be employed in carrying out examples in accordance with this disclosure. Different types and combinations of sensor or other portable electronics devices, computers including clients and servers, implants, and other systems and devices can be employed in examples according to this disclosure.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided.

Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more" In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure.

This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

NOTES AND EXAMPLES

The above description and the drawings sufficiently illustrate specific examples to enable those skilled in the art to practice them. Other examples may incorporate structural, process, or other changes. Portions and features of some examples may be included in, or substituted for, those of other examples. Examples set forth in the claims encompass all available equivalents of those claims. The following, non-limiting examples, detail certain aspects of the present subject matter to solve the challenges and provide the benefits discussed herein, among others.

Example 1 is a cutting guide for a robotic surgical system, the cutting guide comprising: a cutting block defining a guide surface to guide a cutting instrument along a trajectory; an arm connected to the cutting block to couple the cutting guide to the robotic surgical system; and a first retractable shield configured to extend from a first retracted position clear of the trajectory to a second deployed position within the trajectory.

In Example 2, the subject matter of Example 1 includes, a distal surface of the cutting block into which the guide surface extends, wherein in the second deployed position the first retractable shield defines an encirclement zone between the distal surface and the first retractable shield configured to at least partially surround a bone structure to limit translation of the cutting instrument along the guide surface with respect to the bone structure.

In Example 3, the subject matter of Example 2 includes, wherein the first retractable shield includes a first inner surface, the first inner surface correspondingly shaped to engage a first end surface of the cutting block.

In Example 4, the subject matter of Example 3 includes, wherein the first end surface of the cutting block forms a convex shape and the first inner surface of the first retractable shield forms a concave shape.

In Example 5, the subject matter of Example 4 includes, wherein the first retractable shield includes a first outer surface forming an ellipsoidal shape.

In Example 6, the subject matter of Examples 4-5 includes, an electric or a pneumatic motor, wherein the first retractable shield is electrically or pneumatically drivable, respectively, between the first retracted position and the second deployed position.

In Example 7, the subject matter of Examples 4-6 includes, a deployment spring, wherein the first retractable shield is spring drivable from the first retracted position to the second deployed position.

In Example 8, the subject matter of Example 7 includes, a lock system engageable with the first retractable shield to maintain the first retractable shield in the first retracted position or in the second deployed position.

In Example 9, the subject matter of Examples 1-8 includes, a door operatively coupled to the first retractable shield, the door configured to inhibit engagement of the cutting instrument with the guide surface when the first retractable shield is in the first retracted position, and enable engagement of the cutting instrument with the guide surface when the first retractable shield is in the second deployed position.

In Example 10, the subject matter of Examples 1-9 includes, wherein the arm includes a first portion engageable with the robotic surgical system, a second portion extending from the first portion at an obtuse angle relative to the first portion, and a third portion extending from the second portion and connected to the cutting block.

In Example 11, the subject matter of Example 10 includes, wherein the second portion of the arm forms a concave shape laterally and vertically offsetting the first portion of the arm from the third portion of the arm.

Example 12 is a cutting guide connectable to a robotic surgical system for guiding resection of a femoral neck during a robotically assisted hip replacement procedure, cutting guide comprising: a cutting block including a first end surface defining a first curved axis and a distal surface into which a guide surface extends to guide a cutting instrument along a trajectory during resection of the femoral neck; an arm connected to the cutting block to couple the cutting guide to a robotic surgical system; and a first retractable shield connected to the cutting block and translatable proximally and distally along the first curved axis between a first retracted position and a second deployed position, respectively, in which second deployed position the first retractable shield defines an encirclement zone between the distal surface and the first retractable shield configured to at least partially surround the femoral neck to secure the cutting block to the femoral neck and limit translation of the cutting instrument along the guide surface with respect to the femoral neck.

In Example 13, the subject matter of Example 12 includes, a second retractable shield connected to the cutting block and translatable proximally and distally along a second curved axis defined by a second end surface of the cutting block between a first retracted position and a second deployed position, respectively, in which second deployed position the second retractable shield at least partially defines the encirclement zone.

In Example 14, the subject matter of Example 13 includes, at least one deployment spring and at least one retraction spring, wherein the first retractable shield and the second retractable shield are spring drivable from the first retracted position to the second deployed position, and wherein the first retractable shield and the second retractable shield are spring retractable from the second deployed position to the first retracted position.

In Example 15, the subject matter of Examples 13-14 includes, a lock system engageable with the first retractable shield and the second retractable shield to maintain the first retractable shield and the second retractable shield in the second deployed position.

In Example 16, the subject matter of Examples 13-15 includes, wherein the first retractable shield includes a first inner surface and the second retractable shield includes a second inner surface, the first inner surface correspondingly shaped to engage the first end surface of the cutting block and the second inner surface correspondingly shaped to engage the second end surface of the cutting block.

In Example 17, the subject matter of Example 16 includes, wherein the first inner surface and the second inner surface each define a plurality of teeth engageable with a first gear and a second gear, respectively, the first gear and the second gear extending laterally beyond the first end surface and the second end surface, respectively.

In Example 18, the subject matter of Examples 13-17 includes, wherein the guide surface comprises a slot extending longitudinally through the cutting block between the distal surface of the cutting block and a proximal surface of the cutting block.

In Example 19, the subject matter of Example 18 includes, a door operatively coupled to the first retractable shield or the second retractable shield, the door configured to inhibit insertion of the cutting instrument into the slot when the first retractable shield or the second retractable shield are in the first retracted position and enable insertion of the cutting instrument into the slot when the first retractable shield or the second retractable shield are in the second deployed position.

Example 20 is a method of resecting a femoral neck during a robotically assisted hip replacement procedure, the method comprising: using processing circuitry, controlling movement of a robotic surgical arm to position a distal surface of a cutting block of a cutting guide extending from the robotic surgical arm proximate a proximal side of the femoral neck to locate a guide surface defined by the cutting block along a trajectory; translating a first retractable shield connected to the cutting block distally from a first retracted position to a second deployed position around a distal side of the femoral neck; engaging a cutting instrument with the guide surface defined by the cutting block to contact the femoral neck; and resecting the femoral neck by activating and translating the cutting instrument along the guide surface to contact the first retractable shield to limit translation of the cutting instrument with respect to the femoral neck to protect soft tissue proximal to the femoral neck.

In Example 21, the subject matter of Example 20 includes, wherein translating the first retractable shield includes translating a second retractable shield connected to the cutting block distally from a first retracted position to a second deployed position to secure the distal surface of the cutting block to the femoral neck.

In Example 22, the subject matter of Example 21 includes, wherein resecting the femoral neck includes resecting the femoral neck by activating and translating the cutting instrument along the guide surface to contact the second retractable shield to limit translation of the cutting instrument with respect to the femoral neck to protect soft tissue proximal to the femoral neck.

In Example 23, the subject matter of Example 22 includes, wherein resecting the femoral neck includes translating the cutting instrument distally along the guide surface to contact the first retractable shield or the second retractable shield to limit vertical translation of the cutting instrument with respect to the femoral neck to protect soft tissue proximal to the femoral neck.

In Example 24, the subject matter of Examples 20-23 includes, wherein translating the first retractable shield is accomplished using processing circuitry of the robotic surgical arm to cause the first retractable shield to translate distally under electric or pneumatic assistance.

In Example 25, the subject matter of Examples 20-24 includes, wherein translating the first retractable shield is accomplished by operating a lock to cause the first retractable shield to translate distally under spring pressure.

In Example 26, the subject matter of Examples 20-25 includes, wherein translating the first retractable shield causes a door inhibiting engagement of the cutting instrument with the guide surface when the first retractable shield is in the first retracted position to translate with respect to the guide surface to enable engagement of the cutting instrument with respect to the guide surface when the first shield retractable shield is in the second deployed position.

Example 27 is at least one machine-readable medium including instructions that, when executed by processing circuitry, cause the processing circuitry to perform operations to implement of any of Examples 1-26.

Example 28 is an apparatus comprising means to implement of any of Examples 1-26.

Example 29 is a system to implement of any of Examples 1-26.

Example 30 is a method to implement of any of Examples 1-26.

What is claimed is:

1. A cutting guide for a robotic surgical system, the cutting guide comprising:

a cutting block defining a guide surface to guide a cutting instrument along a trajectory and a distal surface into which the guide surface extends;

an arm connected to the cutting block to couple the cutting guide to the robotic surgical system; and a first retractable shield configured to extend from a first retracted position clear of the trajectory to a second deployed position within the trajectory;

wherein in the second deployed position the first retractable shield defines an encirclement zone between the distal surface and the first retractable shield configured to at least partially surround a bone structure to limit translation of the cutting instrument along the guide surface with respect to the bone structure.

2. The cutting guide of claim 1, wherein the first retractable shield includes a first inner surface, the first inner surface correspondingly shaped to engage a first shield guide surface of the cutting block.

3. The cutting guide of claim 2, wherein the first shield guide surface of the cutting block forms a convex shape and the first inner surface of the first retractable shield forms a concave shape.

4. The cutting guide of claim 3, wherein the first retractable shield includes a first outer surface forming an ellipsoidal shape.

5. The cutting guide of claim 3, further comprising an electric or a pneumatic motor, wherein the first retractable shield is electrically or pneumatically drivable, respectively, between the first retracted position and the second deployed position.

6. The cutting guide of claim 3, further comprising a deployment spring, wherein the first retractable shield is spring drivable from the first retracted position to the second deployed position.

7. The cutting guide of claim 6, further comprising a lock system engageable with the first retractable shield to maintain the first retractable shield in the first retracted position or in the second deployed position.

8. The cutting guide of claim 1, further comprising a door operatively coupled to the first retractable shield, the door configured to inhibit engagement of the cutting instrument with the guide surface when the first retractable shield is in the first retracted position, and enable engagement of the cutting instrument with the guide surface when the first retractable shield is in the second deployed position.

9. The cutting guide of claim 1, wherein the arm includes a first portion engageable with the robotic surgical system, a second portion extending from the first portion at an obtuse angle relative to the first portion, and a third portion extending from the second portion and connected to the cutting block.

10. A cutting guide connectable to a robotic surgical system for guiding resection of a femoral neck during a robotically assisted hip replacement procedure, the cutting guide comprising:

a cutting block including a first shield guide surface defining a first curved axis and a distal surface into which a guide surface extends to guide a cutting instrument along a trajectory during resection of the femoral neck;

an arm connected to the cutting block to couple the cutting guide to a robotic surgical system; and a first retractable shield connected to the cutting block and translatable proximally and distally along the first curved axis between a first retracted position and a second deployed position, respectively, wherein in the second deployed position the first retractable shield defines an encirclement zone between the distal surface and the first retractable shield configured to at least partially surround the femoral neck to secure the cutting block to the femoral neck and limit translation of the cutting instrument along the guide surface with respect to the femoral neck.

11. The cutting guide of claim 10, further comprising a second retractable shield connected to the cutting block and translatable proximally and distally along a second curved axis defined by a second shield guide surface of the cutting block between a first retracted position and a second deployed position, respectively, wherein in the second deployed position the second retractable shield at least partially defines the encirclement zone.

12. The cutting guide of claim 11, further comprising at least one deployment spring and at least one retraction spring, wherein the first retractable shield and the second retractable shield are spring drivable from the first retracted position to the second deployed position, and wherein the first retractable shield and the second retractable shield are spring retractable from the second deployed position to the first retracted position.

13. The cutting guide of claim 11, further comprising a lock system engageable with the first retractable shield and the second retractable shield to maintain the first retractable shield and the second retractable shield in the second deployed position.

14. The cutting guide of claim 11, wherein the first retractable shield includes a first inner surface and the second retractable shield includes a second inner surface, the first inner surface correspondingly shaped to engage the first shield guide surface of the cutting block and the second inner surface correspondingly shaped to engage the second shield guide surface of the cutting block.

15. The cutting guide of claim 14, wherein the first inner surface and the second inner surface each define a plurality of teeth engageable with a first gear and a second gear, respectively, the first gear and the second gear extending laterally beyond the first shield guide surface and the second shield guide surface, respectively.

16. The cutting guide of claim 11, wherein the guide surface comprises a slot extending longitudinally through the cutting block between the distal surface of the cutting block and a proximal surface of the cutting block.

17. The cutting guide of claim 16, further comprising a door operatively coupled to the first retractable shield or the second retractable shield, the door configured to inhibit insertion of the cutting instrument into the slot when the first retractable shield or the second retractable shield are in the first retracted position and enable insertion of the cutting instrument into the slot when the first retractable shield or the second retractable shield are in the second deployed position.

18. A cutting guide for a robotic surgical system, the cutting guide comprising:

a cutting block defining a guide surface to guide a cutting instrument along a trajectory;

an arm connected to the cutting block to couple the cutting guide to the robotic surgical system;

a first retractable shield configured to extend from a first retracted position clear of the trajectory to a second deployed position within the trajectory; and a door operatively coupled to the first retractable shield, the door configured to inhibit engagement of the cutting instrument with the guide surface when the first retractable shield is in the first retracted position, and enable engagement of the cutting instrument with the guide surface when the first retractable shield is in the second deployed position.

* * * * *